(12) United States Patent
Kim

(10) Patent No.: US 10,896,757 B2
(45) Date of Patent: Jan. 19, 2021

(54) SYSTEM FOR PREDICTING AN ACUTE EXACERBATION OF CHRONIC OBSTRUCTIVE PULMONARY DISEASE

(71) Applicant: CC & I Research Co., Ltd, Seoul (KR)

(72) Inventor: Sugkyung Kim, Seoul (KR)

(73) Assignee: CC & I RESEARCH CO., LTD, Seoul (KR)

( * ) Notice: Subject to any disclaimer, the term of this patent is extended or adjusted under 35 U.S.C. 154(b) by 859 days.

(21) Appl. No.: 15/458,203

(22) Filed: Mar. 14, 2017

(65) Prior Publication Data

US 2018/0239872 A1     Aug. 23, 2018

(30) Foreign Application Priority Data

Feb. 22, 2017   (KR) ........................ 10-2017-0023312

(51) Int. Cl.
*G06F 17/16*   (2006.01)
*G16H 50/20*   (2018.01)
*G16H 50/50*   (2018.01)
*G16H 50/80*   (2018.01)

(52) U.S. Cl.
CPC ............. *G16H 50/20* (2018.01); *G16H 50/50* (2018.01); *G16H 50/80* (2018.01)

(58) Field of Classification Search
CPC combination set(s) only.
See application file for complete search history.

*Primary Examiner* — Scott Luan
(74) *Attorney, Agent, or Firm* — Goldilocks Zone IP Law

(57) ABSTRACT

Provided is a system for predicting an acute exacerbation of COPD. The system, combined with a stored application, including a collection unit gathering variables from a medical record integration server, a virus information server, a weather data server, and a social data server and generating specifications constituted of a data set including of the variables at every point of time when the variables occurred in response to a prediction request on the occurrence of an acute exacerbation of COPD in patient, a model configuration unit determining variables and coefficients of the parameters connected to the variables to set a prediction model, an analysis unit inputting the variables of the specification and the parameter coefficients to the model set by the model configuration unit to predict an occurrence of the acute exacerbation of the COPD in patient, a providing unit providing a prediction result value to at least one client.

12 Claims, 5 Drawing Sheets

[FIG. 1]
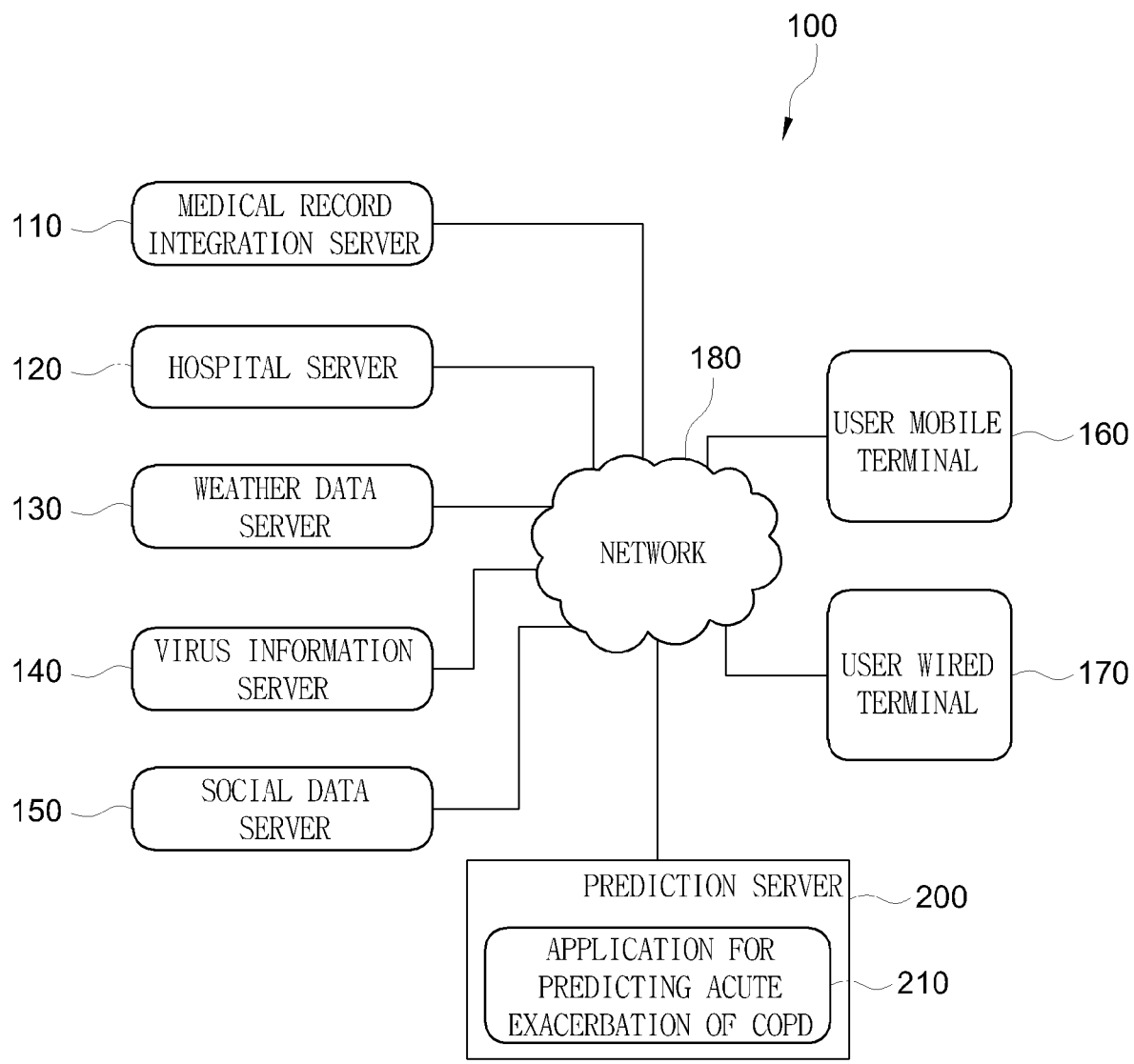

【FIG. 2】
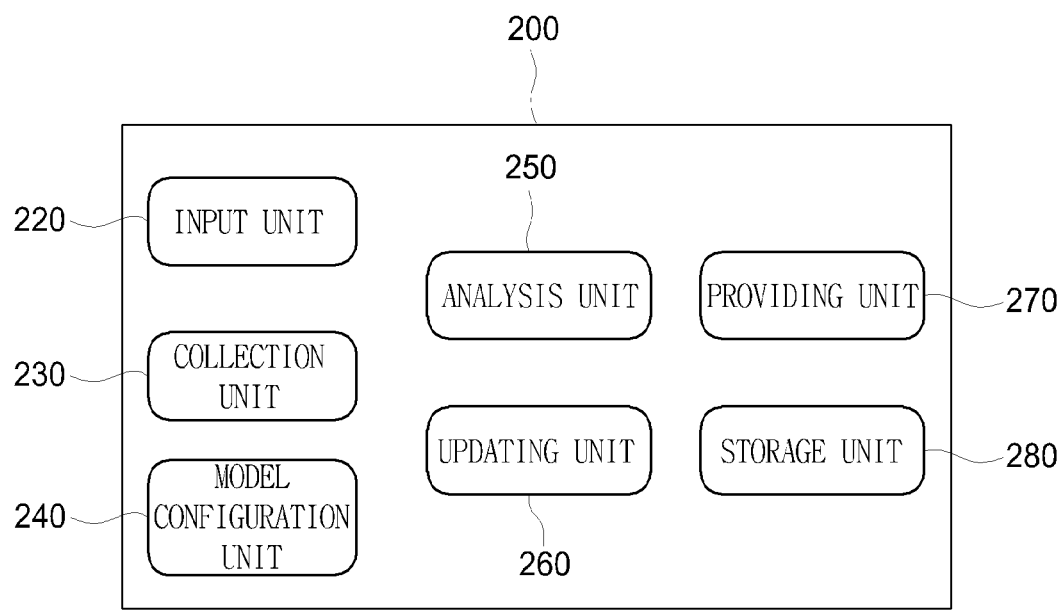

[FIG. 3]
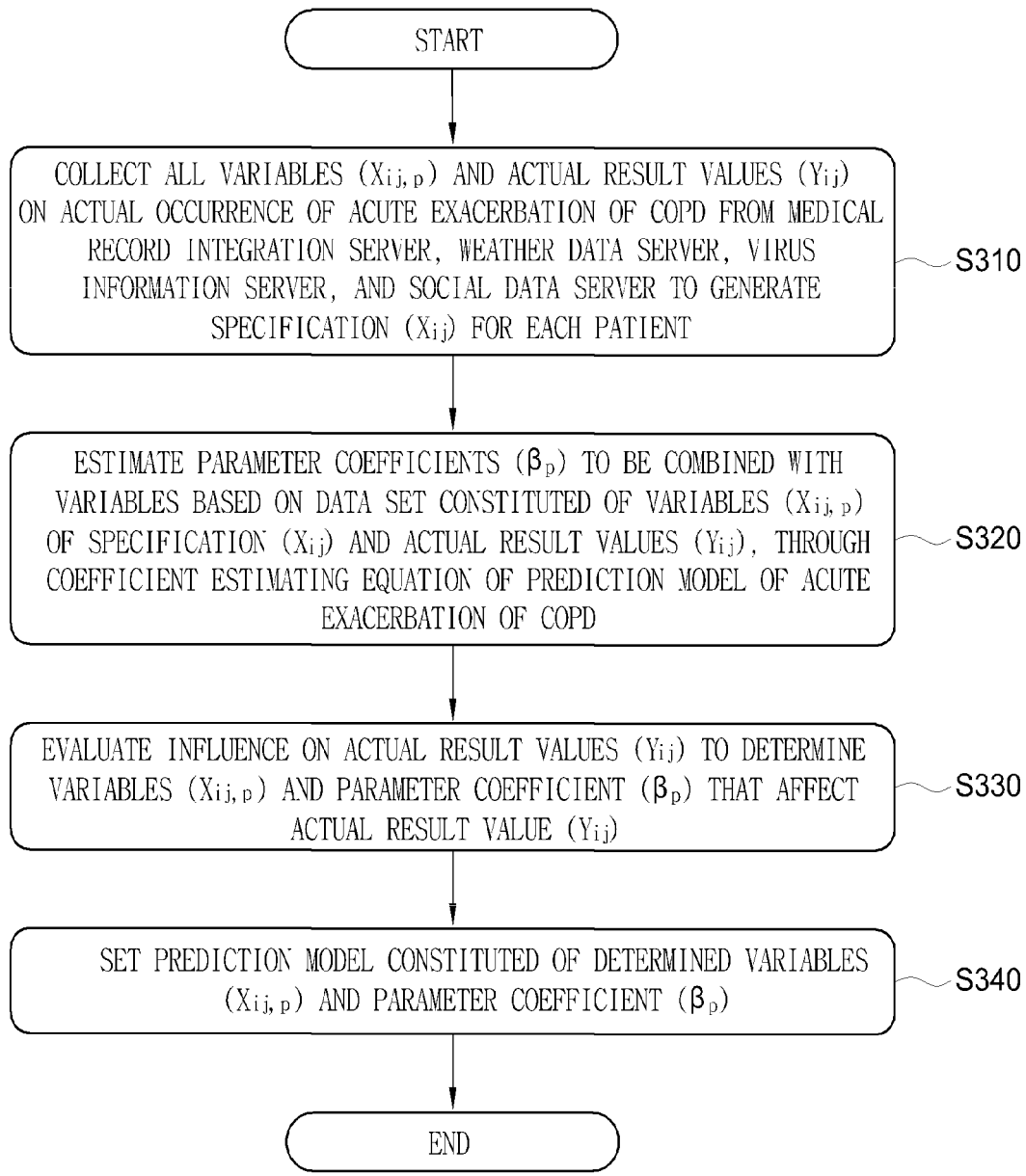

[FIG. 4]
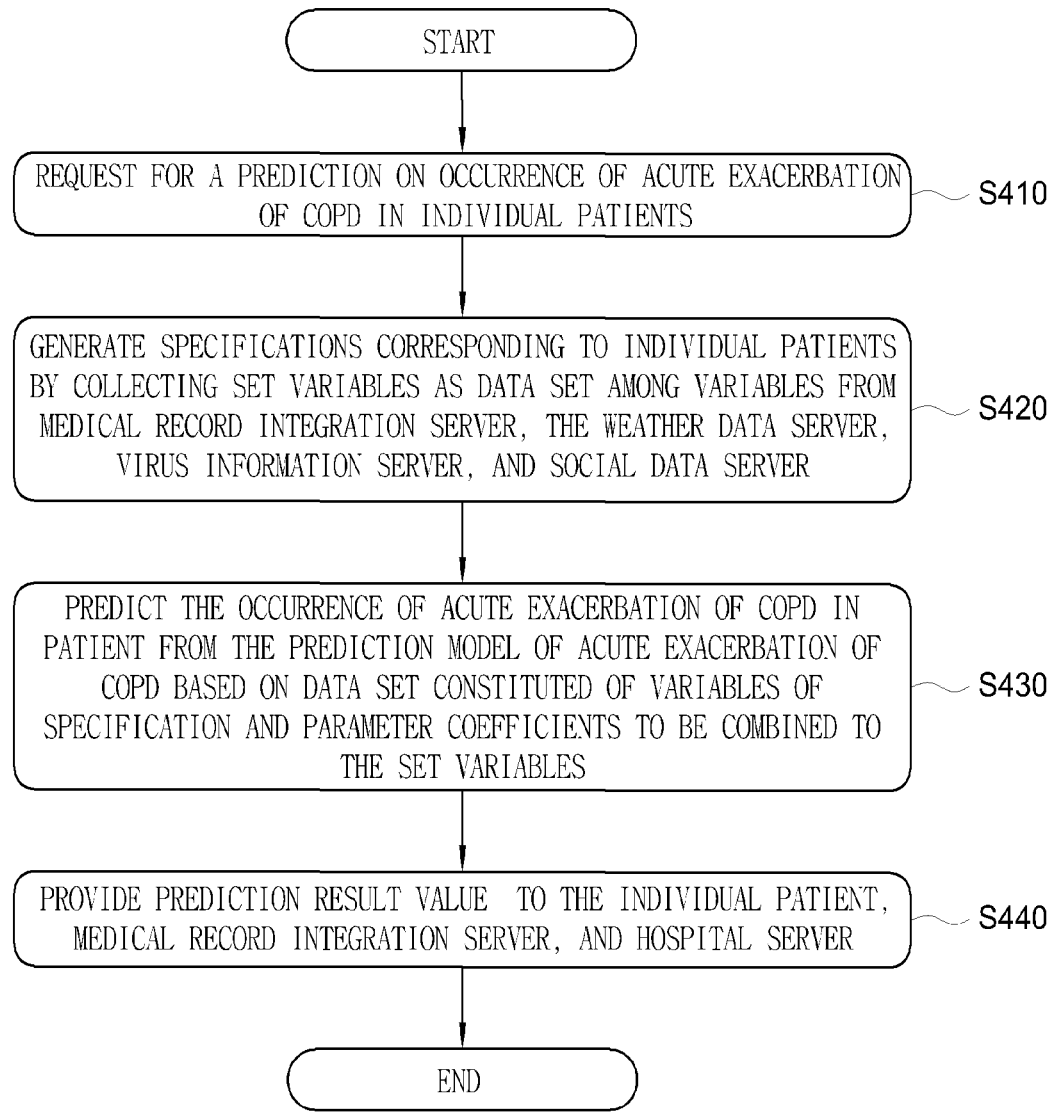

[FIG. 5]
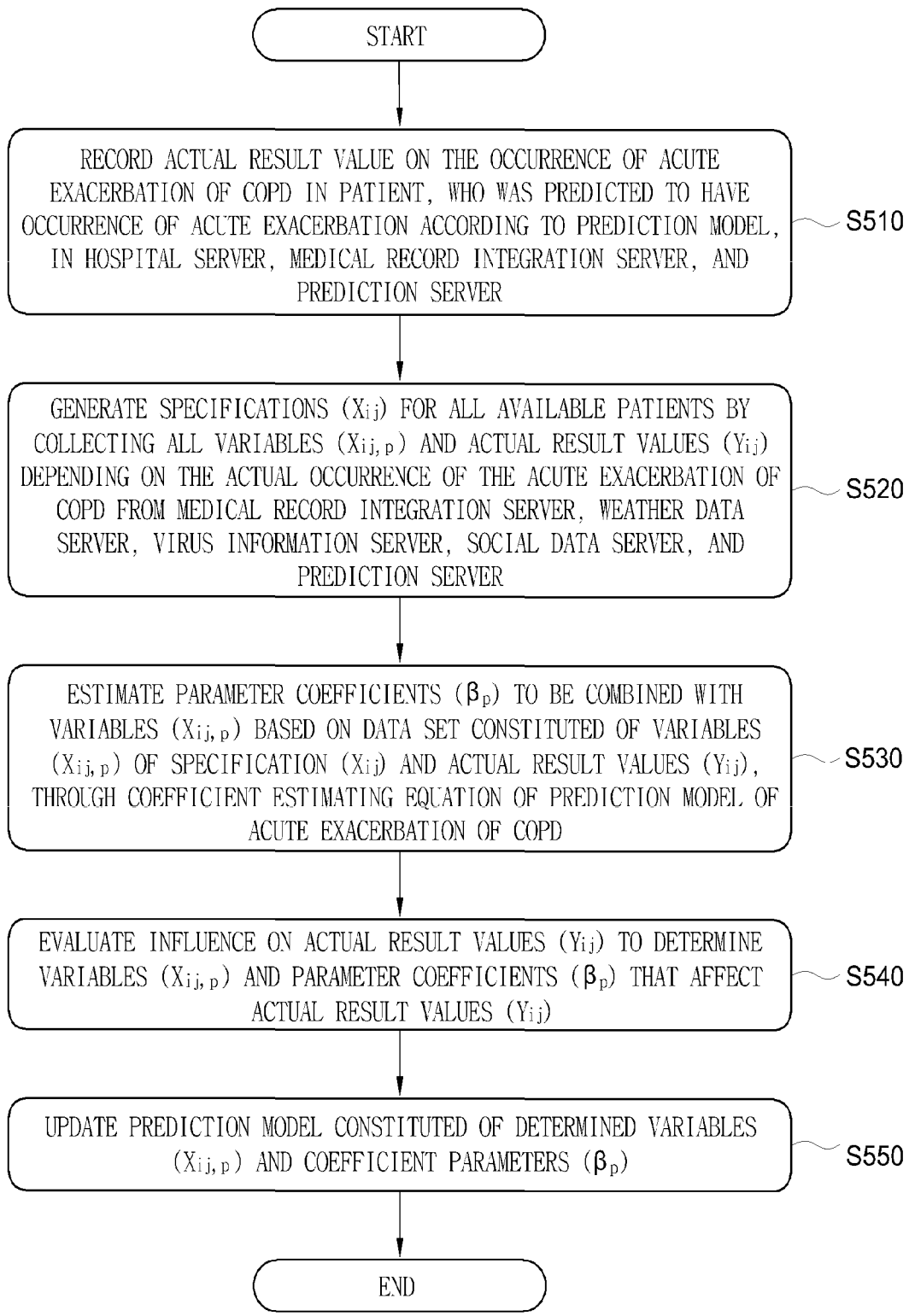

SYSTEM FOR PREDICTING AN ACUTE EXACERBATION OF CHRONIC OBSTRUCTIVE PULMONARY DISEASE

CROSS-REFERENCE TO RELATED APPLICATION

This application claims priority to and the benefit of Korean Patent Application No. 10-2017-0023312, filed on Feb. 22, 2017, the disclosure of which is incorporated herein by reference in its entirety.

BACKGROUND

1. Field of the Invention

The present invention relates to a system for predicting an acute exacerbation of chronic obstructive pulmonary disease (COPD). More particularly, the present invention relates to a system that a patient may use to prevent an acute exacerbation of COPD in him or herself before the event occurs by predicting an acute exacerbation of COPD in individual patients on the basis of a massive data on all available COPD patients from national institutions or insurance companies that integrally manage information of all available hospitals, without being limited to information of COPD patients stored in the hospitals.

2. Discussion of Related Art

Chronic obstructive pulmonary disease (hereinafter, referred to as 'COPD') is a disease in which chronic bronchitis, emphysema which is a disease that causes a damage to alveolar structure, or a mixture of both appears and the airway from bronchus to alveoli closes. Symptoms of this disease include a prolonged coughing with sputum, a decreased air velocity due to airway obstruction causing dyspnea, and frequent respiratory infections such as a common cold. This disease is globally causing a high death rate, and is increasing rapidly due to smoking, air pollution, etc. The cause of COPD is an abnormal chronic inflammatory reaction of the lung to toxic molecules or gases, and various factors, such as smoking, urbanization, pollution, infectious respiratory diseases, etc., are complexly involved in COPD.

An acute exacerbation of COPD can be suppressed through continuous treatment even when COPD develops, but an irregularity in use of medication, a rapid increase of fine dust, a late detection of directly related symptoms connected to COPD, a sudden occurrence of a respiratory virus, a rapid temperature change, and the like may lead COPD patients to rapidly attenuate and die in a short period.

Therefore, it is desirable to reduce a damage caused by such an exacerbation by predicting and preventing the occurrence of the acute exacerbation of COPD in patient or by starting early treatment of symptoms thereof.

To this end, a combination of clinical parameters has been used to predict an acute exacerbation of COPD in patients. But these clinical parameters are not sufficiently accurate to be applied to predictions for individual cases. Furthermore, the COPD patients cannot predict the possibility of acute exacerbation themselves, even though they may have been exposed to a possibility of an acute exacerbation after visits to hospitals due to the aforementioned factors. Therefore, the visit to the hospital by the COPD patient after the occurrence of acute exacerbation of COPD in patient may end up with undesirable result. Hence, it is necessary to develop a tool that allows the patient to predict the possibility of the acute exacerbation of COPD, even before his or her visit to a hospital.

SUMMARY OF THE INVENTION

The present invention is directed to a system that a patient can use to prevent an acute exacerbation of chronic obstructive pulmonary disease (COPD) before the acute exacerbation of COPD occurs in patient, by predicting the occurrence in individual patient on the basis of a massive data on all available COPD patients, such as information from national institutions or insurance companies that integrally manage information of all available hospitals.

The objects of the present invention are not limited to the above-mentioned objects, and other objects not mentioned herein should be obvious to those skilled in the related art in conjunction with the following description.

According to one embodiment of the present invention, there is provided a system for predicting an acute exacerbation of COPD. The system, combined with a stored application, comprising of: an input unit receiving a request from a patient for prediction on an occurrence of an acute exacerbation of COPD in patient; a collection unit gathering variables from a medical record integration server for collecting patient medical information from all available hospital servers that store medical history data and clinical aspect data of COPD patients, a virus information server, a weather data server, and a social data server and generating at least one specification constituted of a data set comprising of the variables at every point of time when the variables selected by a prediction model of the patient occurred in response to a prediction request on the occurrence of an acute exacerbation of COPD in patient from the input module; a model configuration unit determining variables and coefficients of the parameters connected to the variables to set the prediction model for an acute exacerbation of COPD, wherein the variables and coefficients of the parameters are selected from the gathered variables and its connected parameters from the collection unit selected on a predetermined condition; an analysis unit inputting the variables of the specification and the parameter coefficients associate with the variables of the patient to the model set by the model configuration unit to predict an occurrence of the acute exacerbation of the COPD in patient; an updating unit updating the prediction model and providing the updated model to the analysis unit; a providing unit providing a prediction result value to at least one of the members of a group consisting of the patient, the medical record integration server, and the hospital server; and a storage unit storing a prediction result value obtained by the collection unit and an actual result value on the actual occurrence of the acute exacerbation of COPD in the patient, wherein the variables determined on the predetermined condition at least comprise medical history data acquired from the medical record integration server and respiratory virus data acquired from the virus information server, the medical history data at least including a prescribed COPD medication, a frequency of medication intakes, a frequency of emergency room visits, a frequency of hospitalizations, a number of days in care, a number of days on treatment, and a frequency of occurrences of an acute exacerbation of COPD in patient of the COPD patient In another embodiment of the invention, the application of the system for predicting acute exacerbation of COPD is a set of instructions stored within a system for controlling and enabling each of the units of the system.

In another embodiment of the invention, the respiratory virus data is a virus detection rate collected for at least one virus for a predetermined period prior to a certain point of time, at which variables associated to the medical history data or clinical aspect data of the patient are created, and comprise the virus detection rate for at least one of adenovirus (ADV), parainfluenza virus (PIV), respiratory syncytial virus (RSV), H1N1pdm virus, human corona virus (hCoV), human rhion virus (hRV), human boca virus (hBOV), hEV, or IFV.

In another embodiment of the invention, the prescribed COPD medication of the medical history data is a plurality of medications having different ingredients, and the medication intake frequency may be a frequency for each medication.

In another embodiment of the invention, the prediction model uses modeling which reflects that the prediction result value on the occurrence of the acute exacerbation of COPD and the variables are correlated to each other.

In another embodiment of the invention, the prediction model of the acute exacerbation of COPD may use a model that reflects a correlation between a prediction value that indicates the occurrence of the acute exacerbation and the collected variables.

In another embodiment of the invention, the medical history data may further include a frequency of occurrence of the related symptoms, such as asthma, and a frequency of occurrence of an accompanying complications, including at least one of ischemic heart disease, lung cancer, osteoporosis, depression, arthritis, diabetes, gastroesophageal reflux, a pneumothorax, heart failure, hypertension, anemia, or a metabolic syndrome.

In another embodiment of the invention, the clinical aspect data may include at least one of an average smoking amount, a smoking history, a forced expiratory volume in 1 second (FEV1%), or a COPD assessment test (CAT) obtained by quantifying a response to a self-diagnosis questionnaire completed by the patient.

In another embodiment of the invention, the variables used by the system for predicting acute exacerbation of COPD further comprises the variables provided by the weather data server, wherein the weather data is data collected for a predetermined period prior to a certain point of time, at which the variables associated to the medical history data or clinical aspect data of the patient are created, and include at least one of an amount of fine dust accumulation, an amount of minimum temperature accumulation, an amount of change of a minimum temperature, a cumulative amount of precipitation accumulation, an amount of maximum temperature accumulation, an amount of change of a maximum temperature, a daily temperature range, a maximum daily wind speed, an average humidity, or an amount of sunshine.

In another embodiment of the invention, the variables used by the system for predicting acute exacerbation of COPD further comprises the variables provided by the social data server, wherein the social data is data collected for a predetermined period prior to and including a certain point of time, at which variables associated to the medical history data or clinical aspect data of the patient are created, and include at least one of a search frequency of COPD related terms, a search frequency of terms related to the symptoms of COPD, or a search frequency of terms related to a complications accompanied by COPD, which can be found in search engines and social data.

In another embodiment of the invention, the model configuration unit in the system for predicting acute exacerbation of COPD determines parameter coefficients ($\beta$), by obtaining parameter coefficients that solve coefficient estimating equation, in accord with Equation 1, equal to zero.

$$U(\hat{\beta}) = \sum_{i=1}^{N} D_i^T(\beta) V_i^{-1}(\beta, \alpha)\{Y_i - \mu_i(\hat{\beta})\} \qquad \text{[Equation 1]}$$

Wherein i denotes an identifier for each patient, j denotes a specification identifier for each patient, $X_{ij}$ denotes a $j^{-th}$ specification of an $i^{-th}$ patient and is constituted of a data set of variables $\{X_{ij,1}, X_{ij,2} \ldots X_{ij,p}\}$, and $Y_{ij}$ denotes a value of actual results on an acute exacerbation occurrence according to the specification $X_{ij}$, $\beta$ denotes a set of parameter coefficients $\{\beta_0, \beta_1 \ldots \beta_p\}$, wherein the parameter coefficients satisfy relationships of $$D_i(\beta) = \frac{\partial \mu_i(\hat{\beta})}{\partial \beta},$$

$\mu_i(\hat{\beta})$=log it[$\mu_{ij}$], $\mu_{ij}$=E[$Y_{ij}|X_{ij}$] (average), $$V_i(\beta, \alpha) = S_i(\mu_i)^{\frac{1}{2}} R_i(\alpha) S_i(\mu_i)^{\frac{1}{2}},$$

and $S_i(\mu_i)$=diag($V_i$) in case of $V_i$=var($Y_{ij}|X_i$) (dispersion), and $R_i(\alpha)$ denotes a fundamental matrix that is a time varying correlation matrix for solving a correlation between the specification and the value on an acute exacerbation occurrence.

In another embodiment of the present invention, the providing unit in the system of the present invention further records actual result value on the actual occurrence of the acute exacerbation of COPD in the patient who was predicted with the prediction model in the medical record integration server and the prediction server.

In another embodiment of the present invention, the collection unit in the system of the present invention further prepares specifications of all available patients from the collected data of all variables from the medical record integration server, the weather data server, the virus information server, the social data server, and the prediction server and of an actual result values on the actual occurrence of the acute exacerbation of COPD.

In another embodiment of the present invention, the updating unit in the system of the present invention further re-estimates parameter coefficients that associate with the variables, through the coefficient estimating equation of the prediction model based on a data set comprising of the variables of the specification and the actual result values, and evaluates an influence on the actual result values to re-determine the variables and parameter coefficients that affect the actual result values, wherein the re-estimating of the parameter coefficients is executed by obtaining parameter coefficients that solve coefficient estimating equation, in accord with Equation 1, equal to zero.

The specifications on the other embodiment of the present invention are included in the detailed description and the drawings of this application.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings.

FIG. 1 is a schematic diagram illustrating an entire network including a system comprising of a prediction server, in which an application used for predicting an acute exacerbation of chronic obstructive pulmonary disease (COPD) according to an embodiment of the present invention is implemented and stored, a connecting network, a set of wired and wireless user terminals, and a group of servers providing necessary data.

FIG. 2 is a schematic block diagram illustrating each modules of the prediction server with implemented application for predicting an acute exacerbation of COPD.

FIG. 3 is a flowchart illustrating a process constituting the prediction model.

FIG. 4 is a flowchart illustrating a process of predicting an acute exacerbation of COPD in response to a request from a COPD patient.

FIG. 5 is a flowchart illustrating a process of updating a prediction model.

DETAILED DESCRIPTION OF EXEMPLARY EMBODIMENTS

Hereinafter, preferred embodiments of the present invention will be described in detail with reference to the accompanying drawings. However, the present invention is not limited to the embodiments described herein, and other embodiment may exist. The embodiments in the description are provided, so that this disclosure is thorough and complete to fully convey the scope of the present invention to those skilled in the art. Like reference numerals designate like elements throughout the specification. Meanwhile, the terms used herein are used for the purpose of illustrating embodiments and are not intended to limit the present invention. In the present specification, the singular form should be understood to include plural form unless specified otherwise. The terms "comprises" and/or "comprising" used in the specification do not exclude a presence or addition of one or more of other compositions, ingredients, components, steps, operations, and/or elements to the indicated composition, ingredient, component, step, operation, and/or element.

In addition, a "unit" or a "module" used herein generally refers to a component of the present invention, such as logically separable software (a computer program), hardware, or equivalent part. Accordingly, the unit in this detailed embodiment of the present invention includes not only the unit as in a computer program, but also a unit as in a hardware configuration. Thus, the embodiment can also serves as a description for computer program containing instructions, which can be a program for executing each step in a computer, a program for making a computer function as each mean, or a program for making a computer realize each of a function, a system, or a method, in which enables the "unit" or "module." For convenience of description, as used herein, "store," "be stored," or an equivalent term may be used, but these terms refer to a computer program being stored or being controlled to be stored in a storage device, in case of a program. Although individual "modules" and "units" can be configured to have a substantial one-to-one correspondence to a function, in actual practice, a single module may be configured with a single program, a plurality of modules may be configured with a single program, or a single module may be configured as a plurality of programs. A plurality of modules may be executed by a single computer or a single module may be executed by a plurality of computers in distributed or parallel environments. A single module may comprise additional modules. As used herein, the term "connection" includes a logical connection, such as data delivery, instruction, reference relation between data, etc, in addition to a physical connection. As used herein, the term "predetermined" means a condition determined before an object process, and includes not only the condition being set before a start of the process according to the exemplary embodiment of the present invention, but also, as long as done prior to the objective process, being set in regards to a current or a precedent state of the process, according to the exemplary embodiment.

As used herein, the term "system" or "apparatus" may include a plurality of computers, hardware, apparatuses, or the like interconnected via a communication unit, such as a network, including a one-to-one correspondence communication connection, or a single computer, hardware, apparatus, or the like with the processes of the present invention being implemented on.

In addition, for each process, whether a single process being performed by each module or unit or a plurality of processes being performed by each module or unit, target information is read from a storage device, such as memory, and the result of the process is written in the storage device after the process completes. Therefore, there are cases in description, in which a description of reading from the storage device before the process and writing in the storage device after the process may be omitted. The storage device described herein may include a hard disk, a random access memory (RAM), an external storage medium, a storage device via a communication line, a register in a central processing unit (CPU), or the like.

Hereinafter, an application for predicting an acute exacerbation of chronic obstructive pulmonary disease (COPD) according to an embodiment of the present invention will be described in detail with references to FIGS. 1 and 2. FIG. 1 is a schematic diagram illustrating an entire network including a system comprising of a prediction server, in which an application for predicting an acute exacerbation of COPD according to an embodiment of the present invention is being stored and implemented, and FIG. 2 is a schematic block diagram illustrating a prediction server with implemented application for predicting an acute exacerbation of COPD.

Hereinafter, for the convenience of description, the exemplary embodiment of the present invention will be described with a case, in which an application 210 for controlling the prediction server 200 for predicting an acute exacerbation of COPD is implemented in the prediction server 200. However, the application 210 may be mounted on a cloud server or another network server, and may provide services to a user mobile and wired terminal 160 and 170 through a client program, which can interact with the application 210. In addition, respective processes for predicting an acute exacerbation of COPD shown in FIG. 2 may be distributed to and processed by the prediction server 200 and the user terminals 160 and 170.

A system 100 collects medical information, respiratory virus information, weather data, and social data provided by servers, in conjunction with the stored application 210, to construct a prediction model for predicting an acute exacerbation of COPD, and predicts an acute exacerbation of COPD in an individual patient using the said prediction model. The servers, in which provide variables and parameter coefficients used in the prediction model, prediction server 200, in which the application 210 is being integrated, and the user mobile and wired terminals 160 and 170 are provided in the system 100. The said servers may include a medical record integration server 110, a hospital server 120, a weather data server 130, a virus information server 140, and a social data server 150. These components are interconnected through a network 180, either by a wired or wireless connection, and a data exchange between these components is performed via the network 180.

FIG. 1 shows a single component for the each of mobile terminal 160, wired terminal 170, hospital server 120, and social data server 150 for convenience, but each component in FIG. 1 is merely a compressed representative example of the servers of all available hospitals that COPD patients visit, searchable portal sites, social data servers, such as social network services (SNS), message boards, blogs, etc., and user terminals.

The medical record integration server 110 collects patient medical information from all available of hospital servers that store medical history data and clinical aspect data of COPD patients. The medical record integration server 110 is a server that integrally manages patient-specific medical information stored in each hospital, and may be, for example, a server of a national institution or an insurance company. In the case of Republic of Korea, for example, the medical record integration server 110 may be the server of Health Insurance Review & Assessment Service (HIRA).

The hospital server 120 is a server that is installed at the hospital, which an individual COPD patient visits to receive treatments, and may store records of treatments that the COPD patient received from the hospital, prescribed medicines, hospitalization records, diagnostics records, medical examination records, and the likes. The hospital server 120 specifically stores medical history data and clinical aspect data of the individual COPD patients. All available servers of hospitals that treat COPD patients transmit medical history data and clinical aspect data, in which will be described below, to the medical record integration server 110. In addition, the hospital server 120 records information on an occurrence of an actual acute exacerbation of COPD whenever a new medical history data or a new clinical aspect data is created, and transmits the recorded information together with the above described data to the medical record integration server 110.

The medical history data is data on a diagnosis, prescription, and treatment received by the patient due to an acute exacerbation of COPD, and may include a COPD medication intake and its frequency, a frequency of emergency room visits, a frequency of hospitalizations, a number of days in care, a number of days on treatment, a frequency of occurrences of an acute exacerbation of COPD in patient, a record of occurrence related symptoms, a record of occurrence of an accompanying complications, and the like.

The frequency of emergency room visits may be a number of times an emergency room is visited by the patient during the past one or two years, and the frequency of hospitalizations, the number of days in care, the number of days on treatment, and the frequency of occurrences of an acute exacerbation of COPD in patient may also be the data of the patient for each variable for the past one or two years.

The related symptoms may be the symptoms that are directly caused by COPD in the patient during the past one or two years, such as a development of asthma. The accompanying complications may be other diseases that are caused by COPD in patient during the past one or two years, and may include at least one member of a group consisting of an ischemic heart disease, lung cancer, osteoporosis, depression, arthritis, diabetes, gastroesophageal reflux, pneumothorax, heart failure, hypertension, anemia, and metabolic syndrome.

Since prescribed medications differ by the patient's conditions, whether an acute exacerbation of COPD occurs may be determined by the prescribed medication. Accordingly, the COPD medication intake may show a plurality of medicines taken by the patient having different components, and the medication intake frequency of the patient may be a medication intake frequency for each of the medication. Specifically, the medication may be a long-acting muscarinic antagonist (LAMA), a short-acting beta-2 agonist (SABA), a short-acting muscarinic antagonist (SAMA), theophylin, ICSLABA, LABA, sysbronch, SAMASABA, or LABALAMA.

The clinical aspect data may be data on tests and medical examinations conducted on COPD patients in hospitals, and may include at least one of an average smoking amount, a smoking history, a forced expiratory volume in 1 second (FEV1%), or a COPD assessment test (CAT) obtained by quantifying a response to a self-diagnosis questionnaire of the patient. Specifically, the CAT is tallied by numerical responses to questions on the patient's daily coughing, sputum, chest tightness, psychological conditions, etc.

As will be described later in detail, the above-described items of the medical history data and clinical aspect data managed by the medical record integration server 110 are collected by the prediction server 200 in conjunction with the application 210, and are constituted of variables of this specification which are gathered to be used in a prediction model or in a coefficient estimating equation implemented in the prediction server 200. The specification does not employ a point of time at which variables are gathered in the prediction server 200 as its point of generation, but instead employs a point of time at which variables of the medical history data or clinical aspect data are recorded by medical institutions, such as hospitals, as the point of generation.

The weather data server 130 may transmit information on weather that can affect an acute exacerbation of COPD in patient to the prediction server 200.

Variables provided by the weather data server 130 may be data collected for a predetermined period prior to a certain point of time, at which the variables associated to the medical history data or clinical aspect data received by the medical record integration server 110 are created, and may include at least one of an amount of fine dust accumulation, an amount of minimum temperature accumulation, an amount of change of the minimum temperature, or a cumulative amount of precipitation accumulation. For example, the amount of fine dust accumulation, the amount of change of the minimum temperature, the cumulative amount of precipitation accumulation, an amount of maximum temperature accumulation, an amount of change of the maximum temperature, a daily temperature range, a maximum daily wind speed, an average humidity, and an amount of sunshine are the data that are collected from a few days before the creation of the variables in the medical history data or the clinical aspect data, and may be added in the form of variables to the patient's specification corresponding to the point at which the medical history data or clinical aspect data are created.

The virus information server 140 transmits data on a respiratory virus that can affect an acute exacerbation of COPD in patient to the prediction server 200.

The respiratory virus data is a virus detection rate that is collected for a predetermined period, for example, one or four weeks, before the point of time at which variables associated to the patient's medical history data or clinical aspect data are created, and may be data on at least one of adenovirus (ADV), parainfluenza virus (PIV), respiratory syncytial virus (RSV), H1N1pdm virus, human corona virus (hCoV), human rhion virus (hRV), human boca virus (hBOV), hEV, or IFV.

The social data server 150 may be a variety of searchable portal sites or service sites that can enable digital activities performed between the user terminals, including user wireless terminal 160 and user wired terminal 170, for example, message exchange, sharing of text, images, videos, audio, and a variety of data, etc. The service sites may include social network services (SNS), message boards, blogs, and the likes.

The social data server 150 may transmit big data generated from the social media related to an acute exacerbation of COPD obtained in a search engine or the like to the prediction server 200. The big data from social media are the data that are collected for a predetermined time period including the point of time at which variables associated to the patient's medical history data or clinical aspect data are created, and may include search frequencies of COPD related terms, terms related to symptoms caused by COPD, and terms related to complications accompanied by COPD, which are found in data from search engines or social media. The related terms may be, for example, but are not limited to, COPD, asthma, emphysema, chronic bronchitis, dyspnea, acute exacerbations, flu, breathlessness, and the like.

The respiratory virus data and search related social data may be added in the form of variables to the patient's specification corresponding to the point of time at which the medical history data or clinical aspect data are created.

If COPD related trend data is used to predict an acute exacerbation of COPD in patient, a patient can more accurately predict a possibility of an acute exacerbation of COPD in him or herself through indirect understanding of trends and concerns of the other COPD patients.

The user mobile and wired terminals 160 and 170 may be terminals through which a COPD patient can use for external communication, and may include, for example, cellular phones, smart phones, tablet computers, laptop computers, and desktop computers.

The prediction server 200 has the application 210 for predicting an acute exacerbation of COPD stored therein. The application 210 includes instruction sets for operating each unit in prediction server 200, to predict an acute exacerbation of COPD. Specifically, the application 210 includes an instruction set for applying a coefficient estimating equation to estimate parameter coefficients, in which each of the parameter coefficient is associated with each of the variables from the specifications for specific COPD patient that are inputted from each of the servers.

Specifically, the prediction server 200 combined with the application 210, may include an input unit 220, a collection unit 230, a model configuration unit 240, an analysis unit 250, an updating unit 260, a providing unit 270, and a storage unit 280. The input unit 220 receives a prediction request on predicting an occurrence of acute exacerbation of COPD in patient and performs a user authentication.

The collection unit 230 collects variables for constructing a prediction model and variables associated to the requesting COPD patient from each server, and generates a specification constituted of data sets of the variables.

Specifically, the collection unit 230, for the purpose of constructing a prediction model, may acquires a COPD medication intake and its frequency, a frequency of emergency room visits, a frequency of hospitalizations, a number of days on treatment, a frequency of occurrences of acute exacerbation of COPD, a frequency of occurrences of related symptoms, a frequency of occurrences of accompanying complications, a smoking history, FEV1%, CAT, and the like on COPD patient included in variables of the medical history data and the clinical aspect data of all available patients from the medical record integration server 110, and may generates specifications on every point when the variables appeared.

The collection unit 230, for the purpose of constructing a prediction model, may further collect weather information, respiratory virus data, and social data that existed around the creation of the medical history data or the like gathered from the weather data server 130, the virus information server 140, and the social data server 150 into the specification corresponding the point, in which the medical history data is created, as in the form of variables. The collection unit 230 adds the information and data to the specifications.

In addition, the collection unit 230, for the purpose of constructing a prediction model, may further collect information on actual occurrence of an acute exacerbation of COPD in patient for each specification on all available patients, and use a frequency of the occurrences of an acute exacerbation of COPD in patient included in the medical history data.

The specification may be generated every time the medical history data or clinical aspect data is created. In case of differing variables appearing within a predetermined period, a data set of grouped variables appeared within that period may be generated as one specification. If one variable is unchanged while a specific variable varied during that period, the unchanged variable may be re-recorded in a specification generated at the point of the appearance of that specific variable.

The collection unit 230 generates individual patient's specifications, at every point of appearance of the variables, by collecting variables, from each servers, that fits the predetermined condition in response to the patient's request of prediction on occurrence of acute exacerbation of COPD, when the data set of each specification of all available patient and actual result value indicating the actual occurrence of an acute exacerbation of COPD are transmitted to the modeling configuration unit 240 and the prediction model is set.

Meanwhile, the model configuration unit 240 estimates parameter coefficients, wherein each of the said coefficients associate in a predetermined computational form to each of the corresponding variables, using a coefficient estimating equation, and sets the prediction model.

In this case, the prediction model uses the parameter coefficient that associates with each of the corresponding variables and employs variables constituting the dataset of the specification as input values. The prediction model may use modeling that reflects a correlation between a prediction value that indicates the occurrence of an acute exacerbation and the variables, and may be a generalized estimating equation. When an acute exacerbation occurs after the prediction of the acute exacerbation has been made, a prediction result value, an actual result value, and the like may affect the following variables. Therefore the prediction model needs to use the above-mentioned model.

According to the above-described equation, the model configuration unit 240 may input the data set for each of the specifications on all of the patients and the actual result value into the coefficient estimating equation to estimate the parameter coefficients required in the prediction model.

The model configuration unit 240 can determine the variables and the coefficients having high predictability by analyzing the variables constituting the specifications of all available patients, the estimated parameter coefficients, and the actual result values. This analysis is an evaluation of the variables and the coefficients in influences on the actual result values, and may be performed by Pr>|z| or the like required when analyzing dispersion, reliability, and normal distribution of the parameter coefficients.

The model configuration unit 240 determines the variables and parameter coefficients having high predictability among the variables from the data sets of the specifications on all available patients to generate a final prediction model. The final prediction model may be used to predict an acute exacerbation requested by the analysis unit 250.

The above-described prediction model, coefficient estimating equation, and the like will be further described in detail with reference to FIG. 3.

The analysis unit 250 predicts an acute exacerbation of COPD using the prediction model provided to the model configuration unit 240, in response to a prediction request made by a COPD patient through the user wireless terminals 160 and wired terminal 170. The analysis unit 250 calculates a predicted result value of the acute exacerbation based on the specification of the COPD patient who requested the prediction, which is transmitted from the collection unit 230.

After the prediction model is established, the updating unit 260 may update the prediction model by re-analyzing an actual result value of the patient who requested the prediction of the acute exacerbation of COPD and the result value of the acute exacerbation of COPD of a patient who did not made the request.

In this regard, the collection unit 230 can record the actual result value of the patient predicted by the model in the medical record integration server 110 and the storage unit 280, and generate each of the specifications for all available patients by collecting all variables and actual result values on the actual occurrence of acute exacerbation of COPD in patient from the medical record integration server 110, the weather data server 130, the virus information server 140, the social data server 150, and the storage unit 280.

The updating unit 260 may, through the coefficient estimating equation described in the model configuration unit 240, re-estimate parameter coefficients that associate to the variables in a predetermined computational form.

The updating unit 260 may evaluate an influence on the actual result values to re-determine variables and parameter coefficients that affect the actual result values, substantially identical to the above analysis process by the model configuration unit 240. The updating unit 260 provides the updated prediction model to the analysis unit 250.

The providing unit 270 provides the prediction result value obtained by the analysis unit 250 to at least one of the wireless terminal 160 or the wired terminal 170 of the patient, the medical record integration server 110, or the hospital server 120.

The storage unit 280 may store the variables and parameter coefficients that are used in the prediction model together with the prediction result value obtained by the analysis unit 250, and store the actual result value on actual occurrence of acute exacerbation of COPD in patient.

Hereinafter, a process of configuring a prediction model of the embodiment of the present invention conducted by the system for predicting acute exacerbation of COPD with references to FIGS. 1 to 3. FIG. 3 is a flowchart illustrating a process of configuring the prediction model.

First, in operation S310, the collection unit 230 collects all variables $X_{ij,p}$ of all available patients and actual result values $Y_{ij}$ on actual occurrence of acute exacerbation of COPD in patient from the medical record integration server 110, the weather data server 130, the virus information server 140, and the social data server 150, and generates a specification $X_{ij}$ for each of the patients.

Here, i denotes an identifier for each patient, j denotes a specification identifier for each patient, and $X_{ij,p}$ denotes a $p^{-th}$ variable constituting the data set of the specification $X_{ij}$.

Specifically, the collection unit 230 acquires COPD medication intake and its frequency, a frequency of emergency room visits, a frequency of hospitalizations, the number of days on treatment, a frequency of occurrence of acute exacerbation of COPD in the patient, a frequency of occurrences of related symptoms, a frequency of occurrences of accompanying complications, a smoking history, FEV1%, CAT, and the like of COPD from the medical record integration server 110, and generates specifications at every point where the variables make appearance.

In addition, the collection unit 230 adds weather information, respiratory virus data, and social data that existed around the creation of the medical history data or the like to the corresponding specification, from the weather data server 130, the virus information server 140, and the social data server 150 in the form of variables.

The collection unit 230 may collect information on actual occurrence of an acute exacerbation of COPD in patient for each specification of all available patients, and use a frequency of the occurrences of the acute exacerbation of COPD in patient included in the medical history data.

Next, in operation S320, the model configuration unit 240 estimates parameter coefficients βp associates with the variables $X_{ij,p}$ of the specification $X_{ij}$, generated by the collection unit 230, in a predetermined computational form, based on the data sets that are constituted of the variables $X_{ij,p}$ of the specification $X_{ij}$ and the actual result values $Y_{ij}$ through the coefficient estimating equation of the prediction model.

The prediction model constructed by the model configuration unit 240 may use modeling that reflects a correlation between a prediction value indicating the occurrence of acute exacerbation of COPD in patient and the variables. In the present embodiment, a generalized estimating equation is used as the prediction model.

According to the above-described equation, the model configuration unit 240 may estimate the parameter coefficients βp required in the prediction model, by inputting the data set of each specification $X_{ij}$ of all available patient and actual result values $Y_{ij}$ into the coefficient estimating equation.

The coefficient estimating equation follows Equation 1, and parameter coefficients βp are estimated by obtaining solutions of Equation 1 equal to zero.

$$U(\hat{\beta}) = \sum_{i=1}^{N} D_i^T(\beta) V_i^{-1}(\beta, \alpha) \{Y_i - \mu_i(\hat{\beta})\}$$ [Equation 1]

Wherein i denotes an identifier for each patient, j denotes a specification identifier for each patient, $X_{ij}$ denotes a $j^{-th}$ specification of an $i^{-th}$ patient and is constituted of a data set of variables $\{X_{ij,1}, X_{ij,2} \ldots X_{ij,p}\}$, and $Y_{ij}$ denotes a value of actual results on an acute exacerbation occurrence according to the specification $X_{ij}$, β denotes a set of parameter coefficients {β_0, β_1 ... β_p}, wherein the parameter coefficients satisfy relationships of $$D_i(\beta) = \frac{\partial \mu_i(\hat{\beta})}{\partial \beta},$$

$\mu_i(\hat{\beta})=\log \text{it}[\mu_{ij}]$, $\mu_{ij}=E[Y_{ij}|X_{ij}]$ (average), $$V_i(\beta, \alpha) = S_i(\mu_i)^{\frac{1}{2}} R_i(\alpha) S_i(\mu_i)^{\frac{1}{2}},$$

and $S_i(\mu_i)=\text{diag}(V_i)$ in case of $V_i=\text{var}(Y_{ij}|X_i)$ (dispersion), and $R_i(\alpha)$ denotes a fundamental matrix that is a time varying correlation matrix for solving a correlation between the specification and the value on an acute exacerbation occurrence.

Next, in operation S330, the model configuration unit 240 evaluates an influence of values on the actual result values $Y_{ij}$ to determine the variables $X_{ij,p}$ and the parameter coefficients βp that affect the actual result values $Y_{ij}$.

This evaluation analysis is an evaluation on actual result values $Y_{ij}$, and may be performed in Pr>|z| or the like required when analyzing dispersion, reliability, and normal distribution of the parameter coefficients.

Through the evaluation analysis, the present inventor found that variables that significantly affect the occurrence of an acute exacerbation of COPD in patient are medical history data, including a medicine intake and its frequency, a frequency of emergency room visits, a frequency of hospitalizations, a number of days on treatment, and a frequency of occurrences of acute exacerbation of COPD in patient, and respiratory virus data.

The respiratory virus data is a virus detection rate collected for a predetermined period prior to the appearance of the variables related to the medical history of the patient, and is related to at least one of ADV, PIV, RSV, H1N1pdm virus, hCoV, hRV, hBOV, or hEV.

Next, the model configuration unit 240 finally sets the prediction model constituted of the determined variables Xij,p and the parameter coefficients βp, and provides the set prediction model to the analysis unit 250.

The prediction model follows Equation 2, and, as described in Equation 1, β is a set constituting the parameter coefficients βp while A is a predicted result value on occurrence of an acute exacerbation of COPD.

$$A_{ij}=X_{ij} \beta \qquad \text{[Equation 2]}$$

According to the present embodiment, it is possible to improve prediction accuracy through predictions based on the variables with substantially high chance of causing an acute exacerbation of COPD in patient, wherein the said variables are selected by evaluating the variables that affects an acute exacerbation of COPD. Further, by adjusting parameter coefficients of the variables with substantially high chance of causing an acute exacerbation of COPD in patient, the effect of the variables on prediction can be further analyzed, resulting more precise prediction of an acute exacerbation of COPD in patient.

In addition, the acute exacerbation of COPD can be more accurately predicted by understanding trend of other patients indirectly, when the variables including the frequencies of COPD related terms, terms related to symptoms caused by COPD, and terms related to diseases according to COPD, wherein the said variables are detected from personalized social data including data from search engines, SNSs, message boards, or blogs, and trends of social data, are utilized as variables in the prediction model.

Hereinafter, a process of predicting an acute exacerbation of COPD in patient, with references to FIGS. 1, 2, and 4, according to an embodiment of the present invention performed in an system for predicting an acute exacerbation of COPD will be described. FIG. 4 is a flowchart illustrating a process of predicting an acute exacerbation of COPD in response to a request of an individual COPD patient.

First, in operation S410, the input unit 220 receives a request from a COPD patient who desires a prediction on occurrence of acute exacerbation of COPD.

Next, in operation S420, the collection unit 230 collects variables satisfying the conditions of operation S330 among variables relevant to the COPD patient who requested the prediction from each of the servers, and generates a specification of the corresponding patient on every point the variables appears.

A data set of the variables constituting a plurality of specifications is configured in substantially the same manner as in FIG. 3.

Next, in operation S430, the analysis unit 250 calculates a prediction result value on the occurrence of acute exacerbation of COPD in the corresponding patient using the data set comprising of the variables of the specification and parameter coefficients satisfying the condition of operation S330 in the prediction model following Equation 2.

Next, in operation S440, the providing unit 270 provides the prediction result value to at least one of the terminals 160 and 170 of the patient who request the prediction, a medical record integration server, and the hospital server 120 of the corresponding patient, and the storage unit 280 stores the prediction result value and related specifications.

According to the present embodiment, by using the prediction model of an acute exacerbation of COPD in patient based on a massive data on all COPD patients stored in the medical record integration server 110 that integrally manages information of all hospitals, the patient him or herself may prevent the exacerbation of COPD in him or herself before the event occurs.

As described in FIG. 3, the occurrence of an acute exacerbation of the disease in patient can be more precisely predicted, because the prediction model incorporates variables related to social data as well as variables having a high influence on the acute exacerbation of the disease in patient.

Hereinafter, a process of updating a prediction model according to an embodiment of the present invention with reference to FIGS. 1, 2, and 5 will be described. FIG. 5 is a flowchart illustrating a process of updating a prediction model.

First, in operation S510, the providing unit 270 records an actual result value on the actual occurrence of an acute exacerbation of COPD in patient, for whom the event was predicted by the model, in the hospital server 120 of the corresponding patient, the medical record integration server 110, and the storage unit 280.

Next, in operation S520, the collection unit 230 receives a predicted actual result value of the patient from the medical record integration server 110 and the storage unit 280 and collects all of the variables $X_{ij,p}$ and the actual result values $Y_{ij}$ on occurrence of the acute exacerbation of COPD in patient from the medical record integration server 110, the weather data server 130, the virus information server 140, the social data server 150, and the storage unit 280, to generates the specifications $X_{ij}$ for all of the patients. The operation of the collection unit 230 is substantially same as that of operation S310 of FIG. 3, and Xij, Xij,p, Yij, and the following βp are substantially the same as names in FIG. 3 as long as there is no contradiction.

Next, in operation S530, the updating unit 260 re-estimates parameter coefficients βp associating with the variables $X_{ij,p}$ of the specification $X_{ij}$ in a predetermined computational form, based on the data sets constituted of the variables $X_{ij,p}$ of the specification $X_{ij}$ and the actual result values $Y_{ij}$, through a coefficient estimating equation same as Equation 1 described in FIG. 3. The re-estimating of the parameter coefficients is executed by obtaining parameter coefficients that solve coefficient estimating equation same as Equation 1 equal to zero.

Next, in operation 540, the updating unit 260 evaluates an influence on the actual result values $Y_{ij}$ to re-determine the variables $X_{ij,p}$ and the parameter coefficients βp that affect the actual result values $Y_{ij}$ in a substantially the same manner as the evaluation analysis described in operation S330 of FIG. 3.

In operation S550, the updating unit 260 updates the prediction model by reflecting the re-determined variables $X_{ij,p}$ and the parameter coefficient βp to the prediction model in accordance with Equation 2.

According to the embodiment of the present invention, the prediction model can be developed to be more precise and unexpected variables can be reflected through tracking the actual occurrence of an acute exacerbation of COPD in the patient predicted by the system through hospital or medical record integration server and adjusting the variables and parameter coefficients of the prediction model based on the result of the prediction.

According to the present invention, a patient him or herself may prevent an exacerbation of COPD before the occurrence of acute exacerbation of COPD in patient by predicting the event on the basis of a massive amount of data on all COPD patients from national institutions or insurance companies that integrally manage information of all available hospitals.

Also, the accuracy of prediction can be improved by making a prediction based on the variables that has substantially high chance of causing the acute exacerbation of COPD in patient.

In addition, the accuracy of prediction can be further improved by detailed analysis on an influence of the variables utilized in the prediction of the acute exacerbation of COPD in patience through adjusting parameter coefficients associated with variables that are likely to cause the event.

Further, by utilizing frequencies of COPD related terms, terms related to symptoms caused by COPD, and terms related to diseases according to COPD derived from personalized social data, such as search engines, SNSs, message boards, or blogs, the occurrence of an acute exacerbation of COPD in patient can be more accurately predicted by comprehending trends of the other COPD patients.

The application 210 for predicting an acute exacerbation of COPD in patient shown in FIG. 2 or the operations according to the embodiments shown in FIGS. 3 to 5 may be recorded in a computer-readable recording medium in the form of a program fulfilling a function. Here, the computer readable recording medium refers to a recording medium that can accumulate information such as data and programs through an electrical, magnetic, optical, mechanical, or chemical interaction, and can be read by a computer. Examples of such recording media includes, for the removable medium, a portable storage, a flexible disk, a magneto-optical disk, a compact disc read only memory (CD-ROM), a compact disc-rewritable (CD-R/W), a digital versatile disc (DVD), a DAT, a memory card, and the like, and for the mounted medium, a solid state disk (SSD), a hard disk, a ROM, and the like.

In the above descriptions, even though all components constituting the embodiment of the present invention are described as being combined into a one functional apparatus, the present invention is not limited to such embodiment. That is, within the scope of the present invention, components may selectively combine to form one or more functional parts. Also, each of the components of the invention may be implemented with corresponding individual hardware in the embodiment, but some or all of the components may be selectively combined and implemented as a computer program having a program module that executes some or all of functions of the combination of one or more hardware devices.

It should be apparent to those skilled in the art that various modifications can be made to the above-described exemplary embodiments of the present invention without departing from the spirit or scope of the invention. Thus, it should be understood that the present invention covers all such modifications that falls within the scope of the appended claims and their equivalents.

What is claimed is:

1. A system for predicting an acute exacerbation of chronic obstructive pulmonary disease (COPD), combined with a stored application, comprising:

an input interface configured to receive a request from a patient for prediction on an occurrence of an acute exacerbation of COPD in patient;

a collector configured to gather variables from a medical record integration server for collecting patient medical information from all available hospital servers that store medical history data and clinical aspect data of COPD patients, a virus information server, and a weather data server, and generate at least one specification constituted of a data set comprising of the variables at every point of time when the variables selected by a prediction model of the patient occurred in response to a prediction request on the occurrence of an acute exacerbation of COPD in patient from the input interface, the specification being generated by collecting respiratory virus data and weather information from the virus information server and the weather data server that exist before and after the medical record is generated and by attaching the respiratory virus data and the weather information to the specification at the time of the occurrence of the acute exacerbation of COPD in a form of variables;

a model configurer configured to determine variables and coefficients of the parameters connected to the variables to set the prediction model for an acute exacerbation of COPD, wherein the variables and coefficients of the parameters are selected from the gathered variables and its connected parameters from the collector selected on a predetermined condition;

an analyzer configured to input the variables of the specification and the parameter coefficients associated with the variables of the patient to the model set by the model configurer to predict an occurrence of the acute exacerbation of the COPD in patient;

an updater configured to update the prediction model and provide the updated model to the analyzer;

a provider configured to provide a prediction result value to at least one of the members of a group consisting of the patient, the medical record integration server, and the hospital server; and a storage configured to store a prediction result value obtained by the collector and an actual result value on the actual occurrence of the acute exacerbation of COPD in the patient, wherein the variables determined on the predetermined condition at least comprise medical history data acquired from the medical record integration server and respiratory virus data acquired from the virus information server, the medical history data at least including a prescribed COPD medication, a frequency of medication intakes, a frequency of emergency room visits, a frequency of hospitalizations, a number of days in care, a number of days on treatment, and a frequency of occurrences of an acute exacerbation of COPD in patient of the COPD patient.

2. The system for predicting an acute exacerbation of COPD of claim 1, wherein the application is a set of instructions stored within a system for controlling and enabling the system.

3. The system for predicting an acute exacerbation of COPD of claim 1, wherein the respiratory virus data is a virus detection rate collected for at least one virus for a predetermined period prior to a certain point of time, at which variables associated to the medical history data or clinical aspect data of the patient are created, and comprise the virus detection rate for at least one of adenovirus (ADV), parainfluenza virus (PIV), respiratory syncytial virus (RSV), H1N1pdm virus, human corona virus (hCoV), human rhion virus (hRV), human boca virus (hBOV), hEV, or IFV.

4. The system for predicting an acute exacerbation of COPD of claim 1, wherein the prescribed COPD medications of the medical history data is a plurality of medications having different ingredients, and the medication intake frequency may be a frequency for each medication.

5. The system for predicting an acute exacerbation of COPD of claim 1, wherein the prediction model uses modeling which reflects that the prediction result value on the occurrence of the acute exacerbation of COPD and the variables are correlated to each other.

6. The system for predicting an acute exacerbation of COPD of claim 1, wherein the medical history data further include a frequency of occurrences of the related symptoms, such as asthma, and a frequency of occurrences of accompanying complications, including at least one of ischemic heart disease, lung cancer, osteoporosis, depression, arthritis, diabetes, gastroesophageal reflux, a pneumothorax, heart failure, hypertension, anemia, or a metabolic syndrome.

7. The system for predicting an acute exacerbation of COPD of claim 1, wherein the clinical aspect data include at least one of an average smoking amount, a smoking history, a forced expiratory volume in 1 second (FEV1%), or a COPD assessment test (CAT) obtained by quantifying a response to a self-diagnosis questionnaire completed by the patient.

8. The system for predicting an acute exacerbation of COPD of claim 1, wherein the variables used by the system for predicting acute exacerbation of COPD further comprises the variables provided by the weather data server, wherein the weather data is data collected for a predetermined period prior to a certain point of time, at which the variables associated to the medical history data or clinical aspect data of the patient are created, and include at least one of an amount of fine dust accumulation, an amount of minimum temperature accumulation, an amount of change of a minimum temperature, a cumulative amount of precipitation accumulation, an amount of maximum temperature accumulation, an amount of change of a maximum temperature, a daily temperature range, a maximum daily wind speed, an average humidity, or an amount of sunshine.

9. The system for predicting an acute exacerbation of COPD of claim 1, wherein the model configuration unit in the system for predicting acute exacerbation of COPD determines parameter coefficients (β) by obtaining parameter coefficients that solve following coefficient estimating equation equal to zero:

$$U(\hat{\beta}) = \sum_{i=1}^{N} D_i^T(\beta) V_i^{-1}(\beta, \alpha) \{Y_i - \mu_i(\hat{\beta})\}$$

wherein i denotes an identifier for each patient;

j denotes a specification identifier for each patient;

$X_{ij}$ denotes a $j^{-th}$ specification of an $i^{-th}$ patient and is constituted of a data set of variables $\{X_{ij,1}, X_{ij,2} \ldots X_{ij,p}\}$;

$Y_{ij}$ denotes a value of actual results on an acute exacerbation occurrence according to the specification $X_{ij}$;

β denotes a set of parameter coefficients $\{\beta_0, \beta_1 \ldots \beta_p\}$, wherein the parameter coefficients satisfy relationships of $$D_i(\beta) = \frac{\partial \mu_i(\hat{\beta})}{\partial \beta},$$

$\mu_i(\hat{\beta})$=log it[$\mu_{ij}$], $\mu_{ij}$=E[$Y_{ij}|Y_{ij}$] (average), $$V_i(\beta, \alpha) = S_i(\mu_i)^{\frac{1}{2}} R_i(\alpha) S_i(\mu_i)^{\frac{1}{2}},$$

and $S_i(\mu_i)$=diag($V_i$) in case of $V_i$=var($Y_{ij}|X_i$) (dispersion); and $R_i(\alpha)$ denotes a fundamental matrix that is a time varying correlation matrix for solving a correlation between the specification and the value on an acute exacerbation occurrence.

10. The system for predicting an acute exacerbation of COPD of claim 1, wherein the provider further records an actual result value on the actual occurrence of the acute exacerbation of COPD in the patient who was predicted with the prediction model in the medical record integration server and the prediction server.

11. The system for predicting an acute exacerbation of COPD of claim 1, wherein the collector further prepares specifications of all available patients from the collected data of all variables from the medical record integration server, the weather data server, the virus information server, and the prediction server and of an actual result values on the occurrence of the acute exacerbation of COPD.

12. The system for predicting an acute exacerbation of COPD of claim 1, wherein the updater further re-estimates parameter coefficients that associate with the variables, through the coefficient estimating equation of the prediction model based on a data set comprising of the variables of the specification and the actual result values, and evaluates an influence on the actual result values to re-determine the variables and parameter coefficients that affect the actual result values, wherein the re-estimating of the parameter coefficients is executed by obtaining parameter coefficients that solve following coefficient estimating equation equal to zero:

$$U(\hat{\beta}) = \sum_{i=1}^{N} D_i^T(\beta) V_i^{-1}(\beta, \alpha)\{Y_i - \mu_i(\hat{\beta})\}$$

wherein i denotes an identifier for each patient;

j denotes a specification identifier for each patient;

$X_{ij}$ denotes a $j^{-th}$ specification of an $i^{-th}$ patient and is constituted of a data set of variables $\{X_{ij,1}, X_{ij,2} \ldots X_{ij,p}\}$;

$Y_{ij}$ denotes a value of actual results on an acute exacerbation occurrence according to the specification $X_{ij}$;

β denotes a set of parameter coefficients $\{\beta_0, \beta_1 \ldots \beta_p\}$, wherein the parameter coefficients satisfy relationships of $$D_i(\beta) = \frac{\partial \mu_i(\hat{\beta})}{\partial \beta},$$

$\mu_i(\hat{\beta})$=log it$[\mu_{ij}]$, $\mu_{ij}$=E$[Y_{ij}|X_{ij}]$ (average), $$V_i(\beta, \alpha) = S_i(\mu_i)^{\frac{1}{2}} R_i(\alpha) S_i(\mu_i)^{\frac{1}{2}},$$

and $S_i(\mu_i)$=diag($V_i$) in case of $V_i$=var($Y_{ij}|X_i$) (dispersion); and $R_i(\alpha)$ denotes a fundamental matrix that is a time varying correlation matrix for solving a correlation between the specification and the value on an acute exacerbation occurrence.

* * * * *